United States Patent [19]
Vogel et al.

[11] Patent Number: 5,925,046
[45] Date of Patent: Jul. 20, 1999

[54] BIPOLAR PINCETTE

[75] Inventors: Max Vogel, Schlatt, Switzerland; Erich Tritt, Jestetten, Germany

[73] Assignee: S & T Marketing AG, Neuhausen am Rheinfall, Switzerland

[21] Appl. No.: 08/799,550

[22] Filed: Feb. 13, 1997

[30] Foreign Application Priority Data

Feb. 14, 1996 [DE] Germany ............................ 296 02 593
Apr. 6, 1996 [DE] Germany ............................ 296 06 409

[51] Int. Cl.$^6$ .................................................. A61B 17/36
[52] U.S. Cl. .................. 606/51; 606/52; 606/205
[58] Field of Search ................... 606/43, 50–52, 606/205; 219/227, 229, 230, 233, 222–225

[56] References Cited

U.S. PATENT DOCUMENTS

| | | | |
|---|---|---|---|
| 4,681,105 | 7/1987 | Tritt ............................................ | 606/52 |
| 4,890,610 | 1/1990 | Kirwan, Sr. et al. ...................... | 606/51 |
| 5,690,847 | 11/1997 | LaValley et al. ......................... | 219/233 |
| 5,746,739 | 5/1998 | Sutter ......................................... | 606/51 |

*Primary Examiner*—Michael Peffley
*Assistant Examiner*—Roy Gibson
*Attorney, Agent, or Firm*—Bachman & Lapointe, P.C.

[57] ABSTRACT

In a bipolar pincette having two pincette arms ($12_a$) which are connected at one end by a holding means and which are electrically insulated from each other, the holding means has two interconnected channel-like profile portions ($24_a$) each of which is provided with two insertion slots or the like guide paths for a respective blade-like region or a gripping blade (20) of one of the pincette arms ($12_a$) and bears against a longitudinal edge of the pincette arm or gripping blade. The channel-like profile portions ($24_a$) are formed from ceramic material or metallic material; the latter is provided with an electrically insulating coating layer.

28 Claims, 1 Drawing Sheet

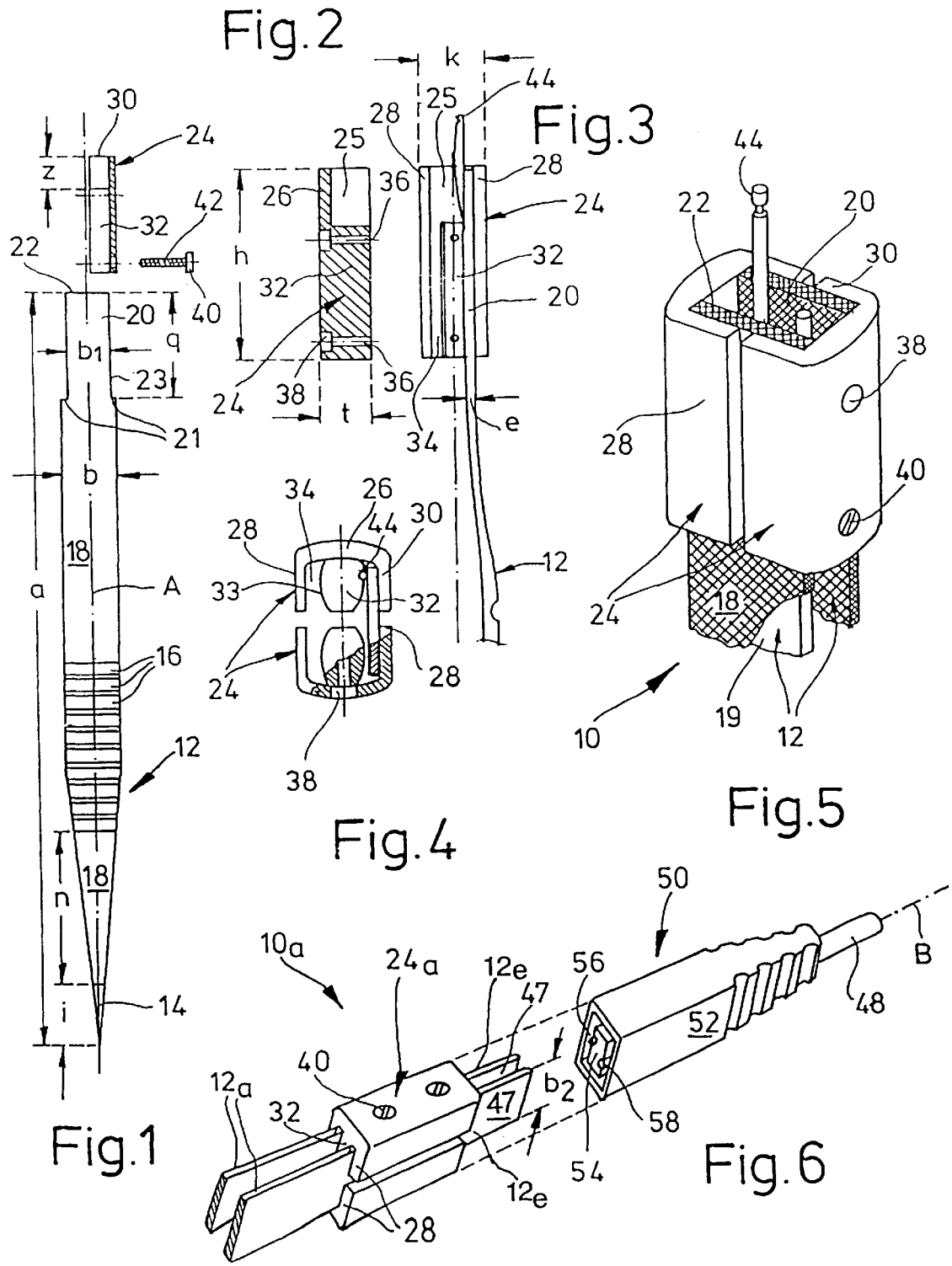

BIPOLAR PINCETTE

BACKGROUND OF THE INVENTION

The invention concerns a bipolar pincette having two pincette arms which at one end are connected by a holding means and which are electrically insulated from each other.

Coagulation pincettes of that kind with pincette arms which each have an insulating sheathing and a tip projecting therefrom are disclosed in the applicants' EP-A-0 092 170. The pincette limbs or arms are insulated relative to each other by an oxide coating which leaves the tips free. It is also described that in principle the sheathing of one of the two pincette arms is adequate for insulation purposes, or an oxide coating at the end remote from the tip of the pincette arms which are there fixed to a metal holder which extends between them and which is of I-shaped cross-section. The ends of the pincette arms project beyond the metal holder and are provided with countersunk bores for contacts to be fitted.

When using a pincette of that kind, in particular in microsurgery, a high-frequency electrical voltage applied to the two pincette arms can be used for example for sclerosing or hardening small blood vessels. However, particularly due to the outwardly disposed contact bores in the free end portions of the pincette arms, it is technically difficult and expensive to provide a current supply which satisfies medical hygiene requirements while affording reliable contact.

Coagulation pincettes are also known, in which the pincette arms are held fast in a plastic body. The use of such coagulation pincettes is possible only to a limited degree as the plastic material does not enjoy adequate resistance to heat, in regard to the required sterilisation procedure.

In consideration of that state of the arts the inventor set himself the aim of substantially improving a bipolar pincette of the kind described in the opening part of this specification in regard to its manufacture, handling and possible uses thereof.

That object is attained in accordance with the teaching of the independent claim; the appendant claims set forth advantageous developments.

SUMMARY OF THE INVENTION

In accordance with the invention the holding means comprises two interconnected channel-like profile portions, each of which is provided with two insertion slots or the like guide paths for a respective blade-like region or a gripping blade of a pincette arm and in the position of use of the pincette bears against a longitudinal edge of the pincette arm or the gripping blade; the two channel profile portions providing the holding means therefore each grip the two pincette arms from a respective longitudinal edge and are held together in that arrangement by screws or the like holding members.

In an embodiment the channel profile members are of metal, preferably an extruded light metal or alloy, and can be provided in turn with an insulating sheath or cover for receiving non-insulated pincette arms.

It has been found desirable in the case of insulated pincette arms to fix thereto a contact pin for making an electrical connection, which engages through the sheathing of the pincette arms and which projects axially beyond the channel profile portion associated with it.

That arrangement provides a compact pincette having a holding means which can serve as a connecting attachment for an electrical plug element which is pushed over the two parallel contact pins and which therefore passes the required current into the pincette arms, in a simple fashion.

The pincette arms of an embodiment of the pincette according to the invention are in per se known manner oxide-coated metal strips with an impressed gripping portion,- the contact pin is welded to the metal core prior to the operation of flame spraying the oxide coating or it is mounted in position after the coating operation; in that case the contact layer must be pierced at the fixing location. The sheathing of the metal strips can be made for example from ceramic material.

A self-insulating holding means which comprises ceramic material, is of particular significance. With such a holding means, the pincette arms can project at the head end; their free ends are then extension blades with current-carrying contact surfaces.

In the case of the channel profile portion according to the invention which comprises metal or ceramic material extending in the interior of the channel configuration is a rib which is formed thereon and whose side walls together with the inside surfaces of the channel walls, define the above-mentioned insertion slots.

In order to simplify the clamping operation for the pincette arms, the side surfaces of the rib can be of a convex configuration so that approximately at the centre of the side, the narrowest location of the insertion slot forms a straight line which is parallel to the longitudinal axis of the pincette.

In accordance with a feature of an embodiment, the rib terminates at a spacing relative to the free end of the channel profile portion and thus defines a head space for receiving the contact pins which are joined to the surface of the pincette arms.

As stated, the two channel profile portions are held together by connecting members, in particular screws, by means of which the spacing between the channel profile portions can also be adjusted.

Moreover, for the sake of easier assembly, the channel profile portions possibly abut against two lateral shoulders of the pincette arms, those shoulders are provided in the longitudinal edges of the pincette arms, more specifically at the transition to the above-mentioned gripping blade.

In connection with the ceramic channel profile portions, it has been found desirable to provide the associated current connection plug with two insertion slots for the above-mentioned extension blades of the pincette; in the interior of the current connection plug which in accordance with the invention is of rectangular cross-section, a terminal block delimits the insertion slots. The terminal block guides contact wires for co-operating with the contact surfaces of the extension blades.

A further configuration of the subject of the invention provides, in the region of the free head space, at the mutually facing free inside surfaces of the gripping blades a contact portion which is free of insulating oxide material and to which can be applied a—possibly resilient—contact pin or the like contact element of a contact plug which can be introduced into the free head space. The contact plug can be disposed releasably in the contact space.

The above-described structure provides in a particularly advantageous manner a current supply for a bipolar pincette, which supply is protected in the optimum fashions which is contact-sure and in particular which is optimised for use under hygienically sensitive conditions.

Overall the invention provides a pincette of simple configuration which can be supplied with current in a bipolar fashion and which is easy to handle and which satisfies all requirements, including those of higher temperatures.

BRIEF DESCRIPTION OF THE DRAWINGS

Further advantages, features and details of the invention are apparent from the following description of a preferred embodiment and with reference to the drawing in which, FIG. 1 is a plan view of a pincette in an exploded condition, FIG. 2 is a view in longitudinal section and on an enlarged scale in comparison with FIG. 1 showing a channel profile portion as part of the pincette, FIG. 3 is a plan view of the channel profile portion, FIG. 4 is a partly sectional plan view onto the free end of the pincette, FIG. 5 is a perspective view of the free end of the pincette, and FIG. 6 is a perspective view of a part of another pincette with associated plug.

DETAILED DESCRIPTION

A pincette 10 of an overall length a of about 130 mm has two strip-like pincette arms 12 which are connected together in parallel relationship, at one end. The free ends of the pincette arms 12 taper to a tip or point 14, of a length i of about 10 mm, which is adjoined at a spacing n of about 27 mm by a gripping region which is formed by a plurality of transverse grooves 16; there the maximum width b of the pincette arm 12 measures about 9 mm. The thickness e of the pincette arm 12, near the gripping portion, is about 0.8 mm; as shown in FIG. 3, that thickness e increases towards the gripping region.

The metallic pincette arm 12 is sheathed with a rough oxide layer of electrically insulating material, which is produced for example by plasma spraying using aluminium oxide. The bare tip 14 projects out of the oxide covering which is shown in exaggerated fashion on a metal core 19 at 18 in FIG. 5.

The other end of the pincette arm 12e in the region of a gripping blade 20, is reduced in cross-section over a length q of about 20 mm to afford a constant width $b_1$, at a dimension of 6.5 mm. That configuration thus provides two shoulder-like steps 21 of which one is arranged on each side of the longitudinal axis A forming a straight line of symmetry. That design configuration affords a spatula-like gripping blade 20 with an end edge 22 which is at a right angle to the longitudinal axis A.

The gripping blade 20 serves to fix two channel profile portions 24 of a length h of 20 mm comprising a channel bottom 26 of an external width k of 6 mm and parallel channel limbs 28 with an external cross-sectional length t of 4 mm; they are fitted in mutually opposite relationship with channel spaces open towards each other, onto the longitudinal edges 23 of the gripping blades.

A rib 32 which is formed centrally in the channel profile portion 24 terminates at a spacing z (about 5 mm) relative to the edge 30, which is remote from the tip of the pincette, of the channel profile portion 24. The rib 32, with the channel limbs 28, defines respective insertion slots 34 for the gripping blades 20 of the two parallel pincette arms 12. For the sake of a better press fit, as shown in FIG. 4 the sides 33 of the ribs are bent in cross-section outwardly in a part-elliptical shape in such a way that the narrowest location of the insertion slot 34 extends approximately at the centre of the rib side 33.

In addition, two screwthreaded bores 36 pass through one of the two ribs 32 of the channel profile portions 24 which supplement each other; aligned therewith in the final position of the pincette 10 are bores 36 in the other rib 32, and they each open into a cylindrical enlargement portion 38. The latter accomodates the head 40 of a screw 42 which holds the channel profile portions 24 together and presses same against the longitudinal edges 23 of the gripping blades.

The entire channel profile portion 24 is made from an aluminium alloy, preferably by extrusion, and anodised, after cutting to length of the portion of the length z of the rib 32. That operation of cutting the rib 32 to length results in the formation of a free head space 25 in the channel profile portion 24; a contact pin 44 which is fixed to the respective metal core 19 in the region of the gripping blade 20 and which provides an electrical contact with the respective metal core 19 extends in the free head space 25.

Accordingly the pincette 10 comprises the two pincette arms 12 and the pair of channel profile portions 24 which hold them and which are screwed together and which at the same time provide a plug holding means for a current connecting plug (not shown in the drawing in relation to this construction); the plug is connected to the above-mentioned contact pins 44 and permits a flow of current through the metal core 19 of the two pincette arms 12 to the tips 14 thereof, which are supplied with current of different polarities.

If the metal channel profile portions 24 are covered with an insulating material the covering layer 18 on the pincette arms can be omitted.

In the case of the pincette 10a in FIG. 6, the channel profile portions $24_a$ are formed from a ceramic material; those channel profile portions $24_a$ hold together the pincette arms $12_a$ of different polarities, like the above-mentioned metal profile portions with an insulating coating. In this case, coating-free extension blades 12e of a width $b_2$ which extend the pincette arms $12_a$ replace the above-described contact pins 44.

A current connection plug 50 of rectangular cross-section, which is disposed at a cable end 48, is pushed onto the extension blades 12c which provide contact surfaces 47. An axial terminal block 54, with the side walls 52 of the plug 50, define insertion slots 56 for the extension blades 12e. Contact wires 58 for making contact with the contact surfaces 47 extend in the terminal block 54 in parallel relationship with the axis B of the cable.

We claim:

1. A pincette for bipolar coagulation comprises:
    a pair of pincette arms extending along a longitudinal axis (A), each pincette arm having a tip on one end and a gripping blade on the other end; a pair of opposed channel profile portions, each channel profile portion receiving at least an edge portion of each gripping blade for securely holding the gripping blades in spaced part relationship thereby defining a space between the gripping blades; and at least two contact pins located at least in part within the space and extending substantially parallel to the longitudinal axis (A) wherein a portion of each of the at least two contact pins axially projects beyond the channel profile portions away from the tip of each pincette arm.

2. A pincette according to claim 1 wherein an insulating block is provided between the pincette arms.

3. A pincette according to claim 1 wherein each of the channel profile portions are formed from metallic material.

4. A pincette according to claim 3 wherein each of the channel profile portions of metallic material are provided with an electrically insulating sheathing layer.

5. A pincette according to claim 4 wherein each of the at least two contact pins is fixed to a pincette arm and passes through the insulating sheathing layer for a current connection plug.

6. A pincette according to claim 5 wherein the insulating sheathing layer comprises ceramic material.

7. A pincette according to claim 1 wherein each of the channel profile portions comprise ceramic material.

8. A pincette according to claim 1 wherein each gripping blade has an extension blade which projects beyond the channel profile portions and has at least one contact surface for a current connection plug.

9. A pincette according to claim 8 wherein each of the channel profile portions include two channel limbs and a rib extending between and parallel to the channel limbs to define insertion slots between the two channel limbs and rib.

10. A pincette according to claim 9 wherein each channel profile portion has a channel bottom and the rib is formed on the channel bottom.

11. A pincette according to claim 9 wherein at least one of the channel limbs and rib defining the insertion slot is convexly curved in part towards the insertion slot.

12. A pincette according to claim 11 wherein the rib has side surfaces and the contours of the side surfaces converge inwardly and are part-elliptical in cross-section.

13. A pincette according to claim 12 wherein the insertion slot is narrowest in cross-section at the center of the rib side surfaces.

14. A pincette according to claim 9 wherein the rib terminates at a spacing (z) relative to the free end of the channel profile portion and delimits a head space.

15. A pincette according to claim 14 wherein a portion of the contact pins extends in the head space.

16. A pincette according to claim 14 wherein in the head space the surfaces of the gripping blades of the pincette arms have a contact portion which is free of the insulating sheathing and to which can be applied a contact element of a current connection plug adapted to be introduced into the head space.

17. A pincette according to claim 16 wherein the contact element is of resilient nature.

18. A pincette according to claim 16 wherein the contact element is releasably disposed in the head space.

19. A pincette according to claim 9 wherein the ribs of the two channel profile portions are provided with aligned passages for connecting members.

20. A pincette according to claim 19 wherein the passages in a channel profile portion are screw holes.

21. A pincette according to claim 19 wherein the passages in a channel profile portion open in an enlargement portion arranged at the outside of the channel bottom for receiving a screw head.

22. A pincette according to claim 9 wherein the length of the channel limbs is shorter than half the width ($b_1$) of each gripping blade of each pincette arm.

23. A pincette according to claim 22 wherein the width ($b_1$) of the gripping blade is shorter than the adjoining width (b) of the pincette arm thereby forming shoulder steps in the pincette arm.

24. A pincette according to claim 23 wherein the shoulder steps are abutments for the channel profile portions.

25. A pincette according to claim 8 wherein the current connection plug has an insertion slot for each of the extension blades and each insertion slot has at least one respective contact wire to co-operate with the contact surface of the extension blade.

26. A pincette according to claim 25 wherein the current connection plug has a terminal block extending therein which delimit the insertion slots, the terminal block carrying the contact wires.

27. A pincette according to claim 1 wherein each channel profile portion is formed from an aluminum alloy covered with an anodized layer.

28. A pincette according to claim 27 wherein the channel profile portion is produced by extrusion.

* * * * *